United States Patent
Grodzki et al.

(10) Patent No.: US 8,878,533 B2
(45) Date of Patent: Nov. 4, 2014

(54) MAGNETIC RESONANCE METHOD AND SYSTEM TO GENERATE AN IMAGE DATA SET

(75) Inventors: David Grodzki, Hannover (DE); Bjoern Heismann, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 424 days.

(21) Appl. No.: 13/245,191

(22) Filed: Sep. 26, 2011

(65) Prior Publication Data

US 2012/0074938 A1    Mar. 29, 2012

(30) Foreign Application Priority Data

Sep. 27, 2010 (DE) .......... 10 2010 041 446

(51) Int. Cl.
G01R 33/48 (2006.01)
G01R 33/34 (2006.01)
A61B 5/055 (2006.01)

(52) U.S. Cl.
CPC ............ G01R 33/4824 (2013.01); A61B 5/055 (2013.01)
USPC .......................... 324/309; 324/307; 324/318

(58) Field of Classification Search
CPC .................................................. G01R 33/4824
USPC ............ 324/307–309, 318; 600/410; 382/131
See application file for complete search history.

(56) References Cited

U.S. PATENT DOCUMENTS

| 5,510,710 | A | 4/1996 | Nauerth |
| 7,622,922 | B2 | 11/2009 | Dannels |
| 2008/0265885 | A1* | 10/2008 | Dannels .......... 324/312 |
| 2010/0261993 | A1* | 10/2010 | van der Kouwe et al. .... 600/410 |
| 2011/0215804 | A1* | 9/2011 | Deimling et al. ........... 324/307 |

OTHER PUBLICATIONS

Grodzki, D. M., Jakob, P. M. and Heismann, B. (2012), Ultrashort echo time imaging using pointwise encoding time reduction with radial acquisition (PETRA). Magn Reson Med, 67: 510-518. doi: 10.1002/mrm.23017.*

"3D Radial Projection Technique With Ultrashort Echo Times for Sodium MRI: Clinical Applications in Human Brain and Skeletal Muscle," Nielles-Vallespin et al., Magnetic Response in Medicine, vol. 57 (2007) pp. 74-83.

"Rapid Single Point (RASP) Imaging," Heid et al., SMR, $3^{rd}$ Annual Meeting (1995) p. 684).

* cited by examiner

*Primary Examiner* — Melissa Koval
*Assistant Examiner* — Rishi Patel
(74) *Attorney, Agent, or Firm* — Schiff Hardin LLP

(57) ABSTRACT

In a magnetic resonance system and method the imaging area is readout by: (a) switching at least two phase coding gradients in respective spatial directions, (b) at the full strength of the phase coding gradients, radiating a non-slice-selective RF excitation pulse, (c) after a time t1 after the last radiated excitation pulse, acquiring echo signals entered as raw data points along the radial k-space trajectory predetermined by the strength of the phase coding gradients, (d) repeating (a) through (c) with different phase coding gradients until k-space corresponding to the imaging area is read out in a first region along radial k-space trajectories, depending on the time t1, and (e) reading out a remainder of k-space that corresponds to the imaging area, that is not covered by the first region of k-space and includes the k-space center, in a different manner than by (a) through (d).

13 Claims, 5 Drawing Sheets

FIG 1 (Prior art)
a)
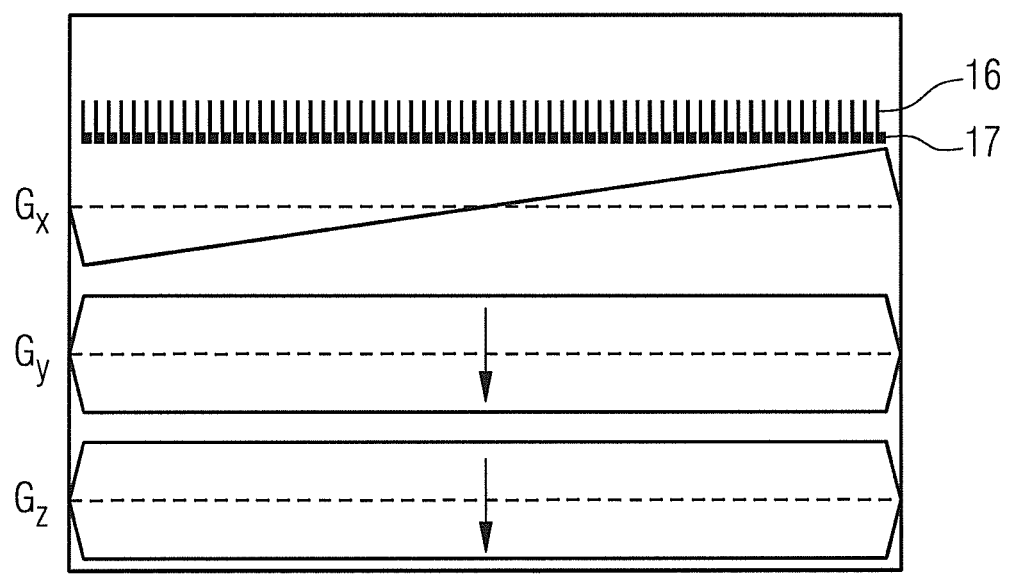
b)
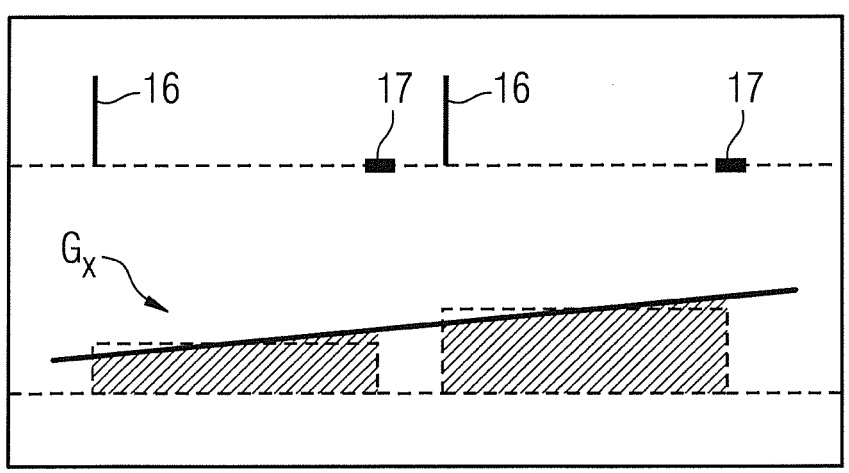

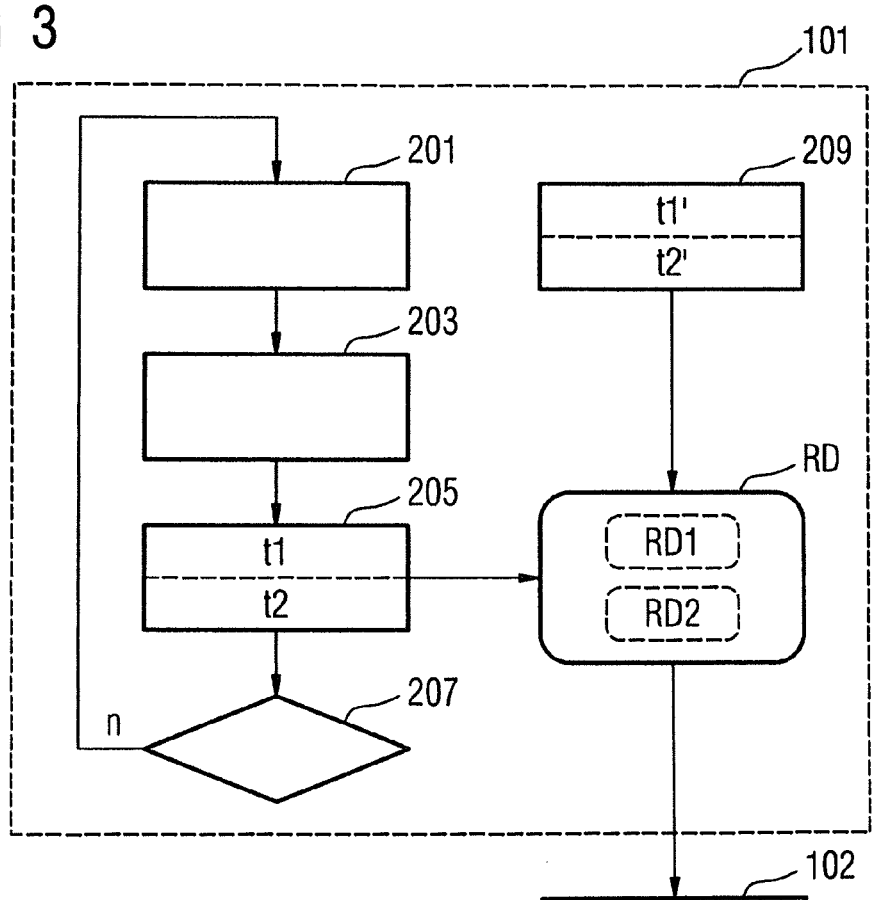
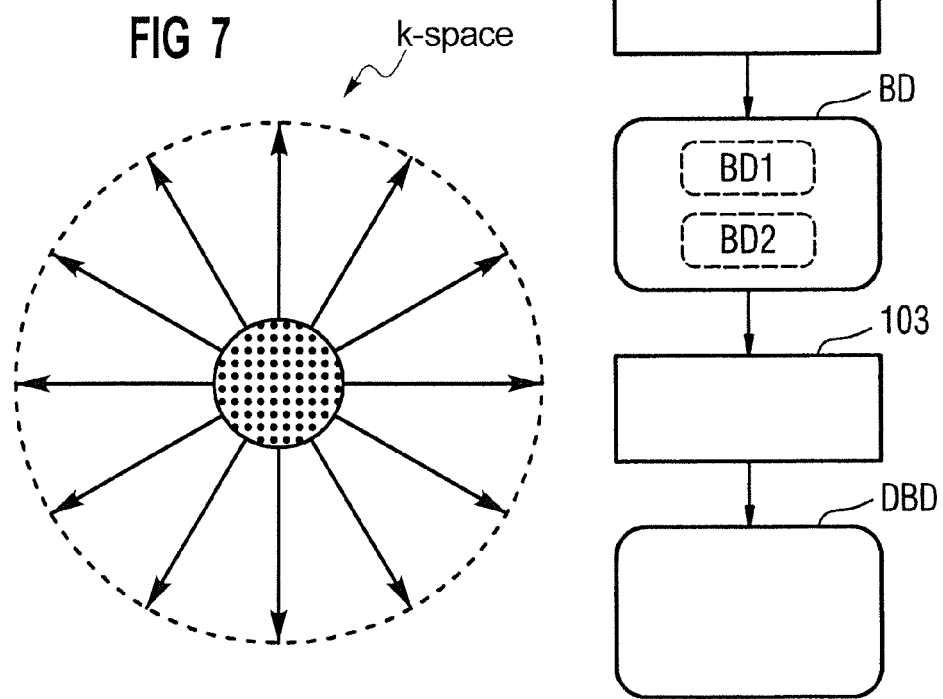

MAGNETIC RESONANCE METHOD AND SYSTEM TO GENERATE AN IMAGE DATA SET

RELATED APPLICATIONS

The present application is related to an application filed Sep. 27, 2011 having Ser. No. 13/245,216 and entitled "Magnetic Resonance System and Method to Automatically Generate a Selective MR Image," (Grodzki), and to an application also filed Sep. 27, 2011 having Ser. No. 13/246,219 and entitled "Magnetic Resonance System and Method to Automatically Generate a Selective MR Image," (Grodzki).

BACKGROUND OF THE INVENTION

1. Field of the Invention

The invention concerns a method in order to generate an image data set by means of a magnetic resonance system. Moreover, the present invention concerns a correspondingly designed magnetic resonance system as well as a corresponding computer program product and an electronically readable data medium.

2. Description of the Prior Art

Magnetic resonance tomography lends itself to new fields of use by the acquisition of MR data with very short echo times TE (for example TE<500 µs). It is thereby possible to show substances or tissue that cannot be depicted by means of conventional sequences, for example a (T)SE ("(Turbo) Spin Echo") sequence or a GRE ("Gradient Echo") sequence, since their T2 time (the relaxation of the transverse magnetization of this substance or tissue) is markedly shorter than the echo time, and thus a corresponding signal from these substances or tissues has already decayed at the point in time of acquisition. With echo times that lie in the range of the corresponding decay time, it is possible for example to show bones, teeth or ice in an MR image although the T2 time of these objects lies in a range from 30-80 µs.

According to the prior art, sequences are known that enable a very short echo time. One example is the radial UTE ("Ultrashort Echo Time") sequence as described, for example, in the article by Sonia Nielles-Vallespin "3D radial projection technique with ultrashort echo times for sodium MRI: Clinical applications in human brain and skeletal muscle", Magn. Res. Med. 2007; 57; P. 74-81. In this sequence type the gradients are ramped up after a wait time T_delay after a non-selective or slice-selective excitation and the data acquisition is begun at the same time. The k-space trajectory scanned in such a manner after an excitation proceeds radially outwardly from the k-space center. Therefore, before the reconstruction (by means of Fourier reconstruction) of the image data from the raw data acquired in k-space these raw data must first be converted into a Cartesian k-space grid (for example by regridding).

An additional approach in order to enable short echo times is to scan k-space in points in that the free induction decay (FID) is detected. Such a method is also designated as a single point imaging since essentially only one raw data point in k-space is acquired for each RF excitation. One example of such a method for single point imaging is the RASP method ("Rapid Single Point (RASP) Imaging", O. Heid, M. Deimling, SMR, 3rd Annual Meeting, Page 684, 1995). According to the RASP method, one raw data point in k-space, the phase of which was coded by gradients, is read out at a fixed point in time after the RF excitation at the "echo time" TE. The gradients are modified by means of the magnetic resonance system for each raw data point or, respectively, measurement point, and thus k-space is scanned point-by-point as is shown in FIGS. 1a and 1 b.

SUMMARY OF THE INVENTION

An object of the present invention is to provide an image data set with a magnetic resonance system, wherein both the echo time and the total measurement time to acquire an image data set are shortened relative to prior art techniques.

There are many applications of magnetic resonance tomography in which it is desired to differentiate different tissue types.

Within the scope of the present invention, a method is provided to create an image data set of an imaging area located in a measurement volume of a magnetic resonance system, the following steps:

read out k-space corresponding to the imaging area, including the steps:

a) switch at least two phase coding gradients (Gx, Gy, Gz) in respective spatial directions by means of a gradient system of the magnetic resonance system, b) after reaching the full strength of the switched phase coding gradients, radiate a non-slice-selective RF excitation pulse by means of an RF transmission/reception device of the magnetic resonance system, c) after a time t1 after the last radiated excitation pulse, acquire echo signals by means of the RF transmission/reception device and store these signals as raw data points along the radial k-space trajectory predetermined by the strength of the phase coding gradients, d) repeats steps a) through c) with different phase coding gradients in each repetition until k-space corresponding to the imaging area is read out in a first region along radial k-space trajectories, depending on the time t1, and e) read out a remainder k-space that corresponds to the imaging area, this remainder not being filled by the first region of k-space including at least the k-space center, in a different manner than as described by steps a) through d), and store these raw data points, and reconstruct image data from the acquired raw data points of k-space by means of an evaluation device of the magnetic resonance system, wherein the reconstruction comprises a Fourier transformation.

By switching the phase coding gradients and waiting until the switched phase coding gradients have reached their full strength before beginning with the RF transmission and the acquisition of echo signals (thus with the acquisition of measurement data), the echo time (the time between the excitation by an RF excitation pulse and the start of the acquisition of the measurement data) can be reduced (for example in comparison to a UTE sequence) in the entirety of k-space to be radially scanned. This is additionally explained below with reference to FIG. 5. Echo signals of substances with very short T2 can therefore also be acquired, and the repetition time (the time between two RF excitation pulses) can also be correspondingly reduced. Moreover, the measurement is less prone to interference (for example eddy currents induced in the gradient system during the changing of its current feed) since nothing is measured during the ramping up of the phase coding gradients. Measurement data can therefore be acquired with more precision.

Because only the region of the k-space center is read out in a different manner from the radial portion in the first region, the measurement time until the entirety of k-space corresponding to the imaging region is scanned is markedly shortened overall, for example relative to pure single point imaging methods.

In an exemplary embodiment, the region of the k-space center ($k_x=0$, $k_y=0$, $k_z=0$) important to the image reconstruction (contrast) is read out in a Cartesian manner, for example by means of a single point imaging method (RASP, for example). The precision of the scanning of the k-space center, and possibly of an area in k-space that surrounds the k-space center, thus can be increased since the raw data read out there already lie on a Cartesian k-space grid, and do not first (like the radially read-out raw data) need to be converted into such data, in a manner prone to error, before image data can be constructed from said raw data.

Overall, a particularly fast method (short measurement time overall) with particularly short echo times is thus obtained (presentation of tissue with small T2 values is possible) via the combination of radial and Cartesian readout of k-space.

In another exemplary embodiment, the time t1, from after the last radiated excitation pulse until the acquisition of the echo signals is started, is equal to the minimum switch-over time $TE_{HW}$ between a transmission mode and a reception mode of the RF transmission/reception device. In the present method the echo time t1 is thus limited at the lower end only by a hardware constant, the switch-over time $TE_{HW}$.

In another exemplary embodiment, three phase coding gradients are switched (activated) in order to acquire a three-dimensional set of raw data and thus to obtain a three-dimensional image data set.

In another exemplary embodiment, precisely two phase coding gradients are switched in order to acquire two sets of raw data to create a projection image data set. With the present method, the total acquisition time for such a set of raw data is short (on the order of a few 100 ms, for example approximately 250 ms), such that a time-resolved presentation of the imaging area is possible.

The advantages and embodiments described with regard to the method apply analogously to the magnetic resonance system in accordance with the invention, which is designed to implement the method described above in any of all embodiments.

The invention also encompasses a non-transitory computer-readable storage medium encoded with programming instructions. The programming instructions, when the storage medium is loaded into a computerized control and evaluation system of a magnetic resonance system, cause the computerized control and evaluation system to implement any or all of the aforementioned embodiments of the method.

BRIEF DESCRIPTION OF THE DRAWINGS

The RASP method known from the prior art is described using FIGS. 1a and 1b.

FIG. 3 is a flowchart of an embodiment of the method according to the invention to create an image data set.

FIG. 7 schematically illustrates k-space filled by radial trajectories in an outer portion and filled in a different manner in an inner portion around the center of k-space.

DESCRIPTION OF THE PREFERRED EMBODIMENTS

A sequence to acquire a line in k-space is shown in FIG. 1a. It can be seen that the two phase coding gradients $G_y$ and $G_z$ are switched with a constant strength while the strength of the third phase coding gradient $G_x$ continuously increases.

The acquisition of two raw data points is shown in detail in FIG. 1b. It is apparent that the echo time—i.e. the time interval from the RF excitation pulse 16 to the beginning of the readout time period 17—is constant. Moreover, the phase coding gradient $G_x$ proceeds in stages from bottom to top. The phase coding gradient $G_x$ for readout of a raw data point is thereby kept constant, which means that the phase coding gradient $G_x$ is kept constant for the time period TE (echo time).

Figure 2:
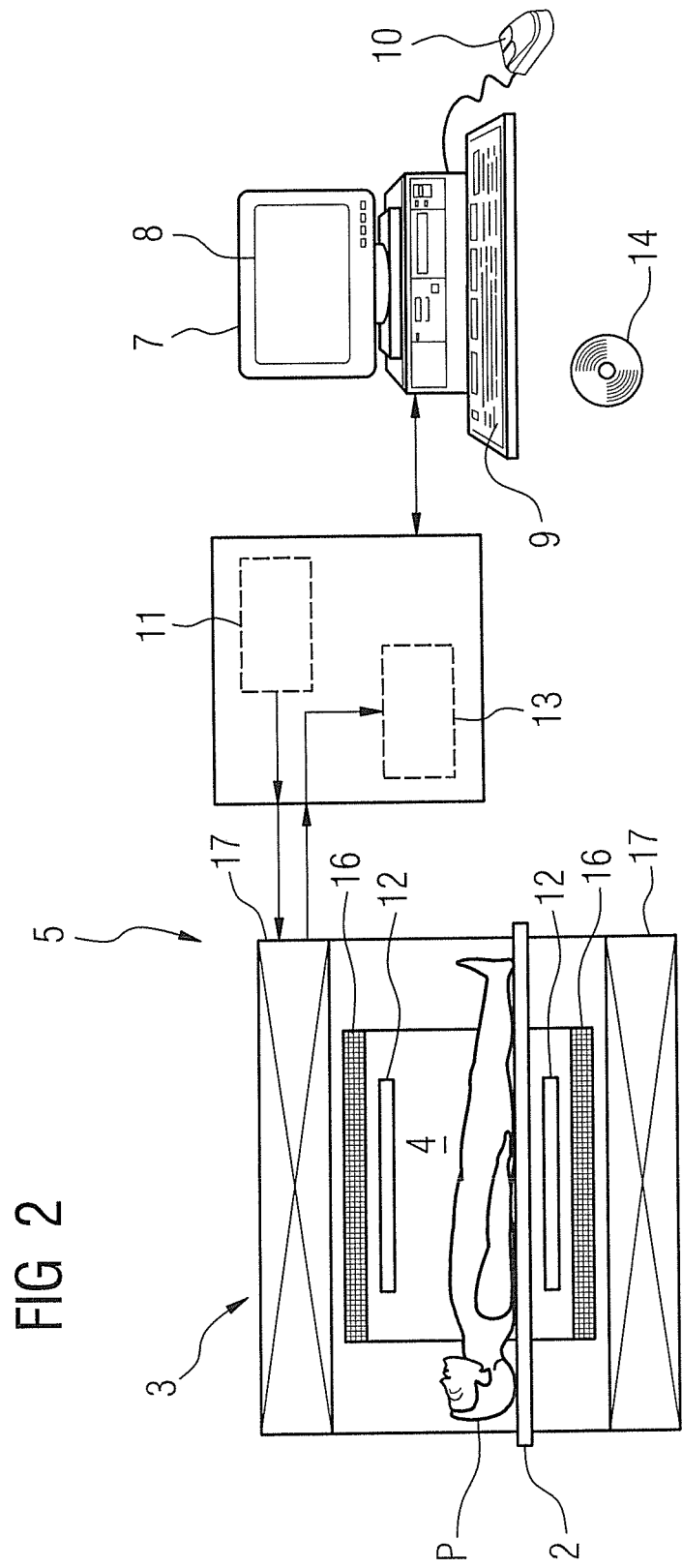
FIG. 2 schematically illustrates a magnetic resonance system according to the invention.

A magnetic resonance system 5 according to the invention is schematically shown in FIG. 2. The magnetic resonance system 5 essentially includes a scanner (data acquisition unit) 3 with a basic field magnet unit 17; and a gradient system 16 with which the magnetic field necessary for the MR examination, including gradient field, is generated in a measurement space 4, a transmission/reception device 12 to transmit RF excitation pulses and receive echo signals, a patient table 2, a control device 6 with which the scanner 3 is operated and raw data are received from the scanner 3, and a terminal 7 connected to the control device 6.

The control device 6 includes an activation unit 11 and an evaluation device 13. During the generation of an image data set, echo signals are acquired by the transmission/reception device 12 by the scanner 3, with the scanner 3 and the table 2 being activated by the activation unit 11 such that MR data are acquired in an imaging area that is located inside the body of a patient P lying on the table 2.

The evaluation device 13 receives the acquired echo signals as raw data and stores and processes these signals. In particular, the evaluation device 13 processes the read-out raw data by exciting a reconstruction algorithm such that the data can be graphically presented on a device (a monitor 8, for example) of the terminal 7, and such that images created according to the invention are displayed. In addition to the graphical presentation of the image data reconstructed from the raw data, with the terminal 7 (which in addition to the monitor 8 has an input device, for example a keyboard 9 and/or a computer mouse 10) a three-dimensional volume segment to be measured can be predetermined as an imaging area by a user, for example, and additional parameters can be defined for implementation of the method according to the invention. The software for the control device 6 can also be loaded into the control device 6 via the terminal 7. This software of the control device 6 can embody control commands for executing one or more embodiments of the method according to the invention. It is also possible for the method according to the invention to be embodied in software that runs in the terminal 7. Independently of the location of the software for implementing the method according to the invention, the software can be stored on a non-transitory, electronically readable data storage medium (a DVD 14, for example) so that this software can then be read from the DVD 14 by the terminal 7 and be copied either into the control device 6 or into a computer of the terminal 7 itself.

A flowchart of an embodiment of the method according to the invention to create an image data set is schematically presented in FIG. 3.

In a first Step 101, k-space corresponding to the imaging area is read out to create an image data set.

For this purpose, at least two phase coding gradients ($G_x$, $G_y$, $G_z$) are switched (activated) in respective spatial directions by means of a gradient system of the magnetic resonance system (Block 201) and a non-slice-selective RF excitation pulse is radiated by means of an RF transmission/reception device of the magnetic resonance system (Block 202). If three phase coding gradients are radiated, a three-dimensional image data set can be reconstructed in a conventional manner from the acquired raw data. If only two phase coding gradients are switched, a projection data set can be reconstructed (as is explained below using FIG. 6).

After a time t1 after the last radiated excitation pulse in which the phase coding gradients switched in Block 201 have already reached their full strength, echo signals are acquired by the RF transmission/reception device and, as raw data points along the radial k-space trajectory predetermined by the strength of the phase coding gradients, are stored as a raw data set RD in an evaluation unit of the magnetic resonance system.

In an embodiment, echo signals are acquired and stored as raw data in the raw data set RD only after the time t1. In a further embodiment, after the time t1 first echo signals are acquired after each RF excitation pulse and stored as raw data in a first raw data set RD1, and furthermore at least one second echo signal is acquired after a time t2 after the same RF excitation pulse and stored as an additional raw data point in a second raw data set RD2, with t2>t1. The second echo signal is generated in a known manner, for example by reversing the polarity of the gradients.

After all desired echo signals have been acquired after an RF excitation pulse, and therefore the corresponding k-space trajectory has been read out, or the corresponding k-space trajectories have been read out, in Step 207 it is checked whether k-space corresponding to the imaging region has thus already been read out or not in a first region of k-space (depending on the time t1) along radial k-space trajectories. If not ("n"), the workflow begins again at Block 201, wherein phase coding gradients different than the previously used phase coding gradients are switched.

K-space corresponding to the imaging area that is not covered (filled) by the first region of k-space (which first region is scanned by means of Blocks 201 through 205) is read out at an arbitrary point in time, or at different points in time between or after the readout of the radial k-space trajectories, for example point-by-point by means of a single point imaging method (RASP, for example) or in another known manner (Block 209), and is likewise stored in the raw data set RD. The raw data points that contain the k-space center thus are acquired in a Cartesian manner; so a regridding of image data before the reconstruction is unnecessary, as shown in FIG. 7.

In the readout of k-space corresponding to the imaging area, the phase coding gradients can be varied continuously between the radiation of a first RF excitation pulse to acquire raw data points of k-space corresponding to the imaging area and radiation of a second RF excitation pulse to acquire additional raw data points of k-space corresponding to the imaging area. This means that the phase coding gradients are not ramped down after each acquisition of a radial k-space trajectory and ramped up again for the acquisition of the next k-space trajectory; rather, the phase coding gradients are only additionally ramped up and down from the already assumed strength until the strength required for the next acquisition is achieved. Eddy currents induced by the current feed of the gradient system that is required to generate the phase coding gradients can thus be reduced, which reduces the formation of noise which is caused by the forces that affect the eddy currents at the gradient system.

It is advantageous to arrange the read-out k-space trajectories such that the strength of the phase coding gradients must only be varied as slightly as possible, whereby the noise caused by the change of the phase coding gradients in the measurement space 4 of the magnetic resonance system can be further reduced.

Analogous to the exemplary embodiments described above, given the raw data points which comprise the k-space center that are read out by means of a different manner (for example by means of single point imaging methods) a raw data point can also either be read out and stored in the first raw data set RD1 only after a first echo time t1' after each RF excitation pulse, or a first raw data point can be read out and be stored in the first raw data set RD1 after a first echo time t1' and a second raw data point can be read out and stored in the second raw data set RD2 after a second echo time t2', with t1'<t2'. The generation of the second echo thereby again takes place in a known manner.

In a further exemplary embodiment, in the cases in which a first and second raw data set RD1 and RD2 were acquired and a first and an additional, second image data set BD1 and BD2 were reconstructed from these, a difference image DBD can be calculated from this first and second image data set BD1 and BD2 (Step 103). Due to the different echo times t1 and t2 with which the first and second raw data set RD1 and RD2 were acquired, it is possible to generate a difference image from the first and second image data set BD1 and BD2 in that tissue with a predetermined T2 is exclusively shown.

For example, such a difference image DBD can take place [sic] via per pixel subtraction of the second image data set BD2 from the first image data set BD1 (or vice versa), possibly with a suitable weighting of at least one of the two image data sets BD1 and BD2, for example: DBD=a*BD1−b*BD2, with weighting factors a and b.

The weighting factors a and b are advantageously dependent on a time constant prevailing in the imaging area imaged with the image data sets BD1 and BD2, in particular depending on the T2 value prevailing in the imaging area. The difference image DBD can therefore be created such that optimally exclusively tissue with a defined (short) T2 is displayed.

Figure 4:
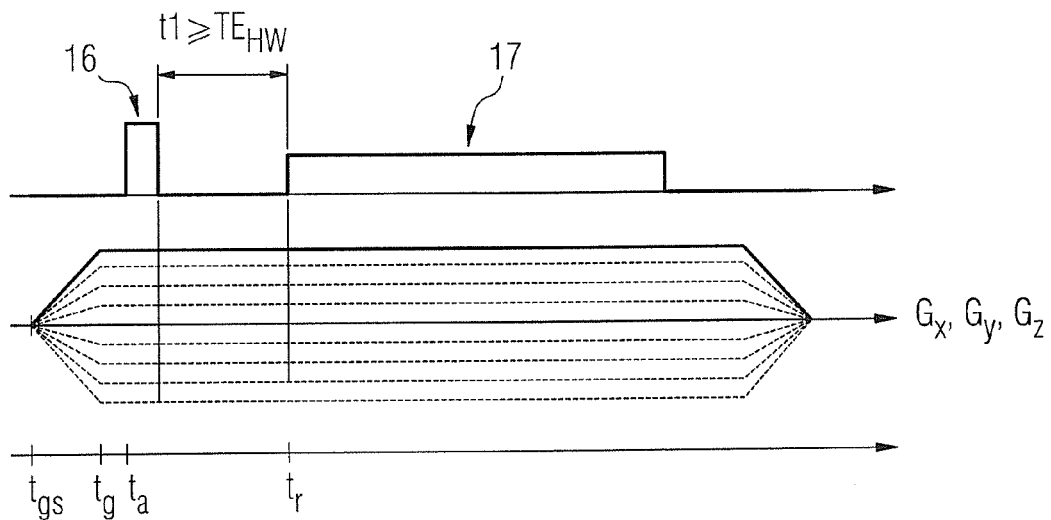
FIG. 4 schematically shows a portion of a sequence to acquire multiple raw data points on a radial k-space trajectory.

The portion of a sequence according to the invention that serves to acquire multiple raw data points on a radial k-space trajectory is schematically shown in FIG. 4 (see FIG. 3, Blocks 201-205). At least two phase coding gradients $G_x$, $G_y$, $G_z$ are ramped up at a point in time $t_{gs}$ and reach their full strength at a point in time $t_g$. An RF excitation pulse 16 is radiated at a later point in time $t_a$>$t_g$. The readout time period 17 to read out the echo signals is begun after an echo time t1 after the RF excitation pulse 16 that corresponds to the hardware-dependent minimum switch-over time between a transmission mode and a reception mode of an RF transmission/reception device $TE_{HW}$ that is used.

In the exemplary embodiment shown in FIG. 4, the phase coding gradients is [sic] switched before the RF excitation pulse is radiated.

Figure 5:
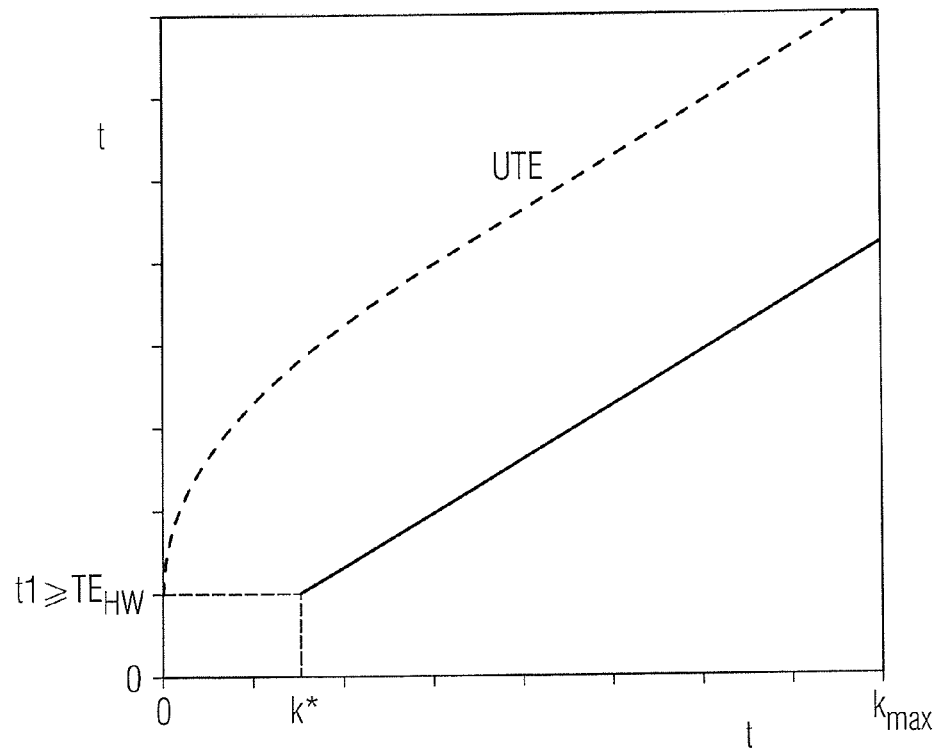
FIG. 5 shows a comparison of k-space values to be read out with a sequence according to FIG. 4 with k-space values to be read out with a UTE sequence, plotted against the respective echo times to be expected.

FIG. 5 shows a comparison of k-space values to be read out with a sequence according to FIG. 4 with k-space values to be read out with a UTE sequence, plotted against the respective echo time to be expected. The k-space values that can be read out with a UTE sequence (in which the ramping of the phase coding gradients is begun simultaneously with the readout of the echoes after the RF excitation pulse) lie on the upper, dashed line.

The k-space values that can be read out with a sequence according to FIG. 4 lie on the lower line in FIG. 5. The comparison of the echo times to be expected against the k-space values of a UTE sequence and the sequence presented in FIG. 4 shows that the echo time in k-space overall is reduced with the sequence shown in FIG. 4, relative to a UTE sequence.

FIG. 5 furthermore shows that the k-space values that can be read out with a sequence according to FIG. 4 first start at a k-space value k* depending on the strength of the applied phase coding gradient, and in particular on the echo time t1. It applies that k*=t1*G, with G being the strength of the gradient.

K-space points in the k-space center are thus not acquired with such a sequence as it is shown in FIG. 4. However, for this these k-points can be acquired on a Cartesian k-space grid—for example point-by-point by means of single point imaging methods—or in another known manner as described in connection with FIG. 3 (Block 209).

In conventional MR acquisitions, either a three-dimensional raw data set is acquired or a slice-selective excitation is used in order to acquire a two-dimensional image data set. Given a slice-selective excitation, a phase coding gradient in the slice direction (also called a slice selection gradient) is switched during the RF excitation pulse, producing a phase that is compensated by inversion of the slice selection gradient after the RF excitation pulse, for example. However, this extends the measurement time per RF excitation pulse. Furthermore, it is also possible to forego a slice resolution and to create a projection image (as is also acquired in x-ray acquisitions, for example). An acquisition of such a projection data set is already possible in a shorter time period with relatively small radial k-space trajectories and the point-by-point Cartesian acquisition in the k-space center. (see FIG. 7).

Figure 6:
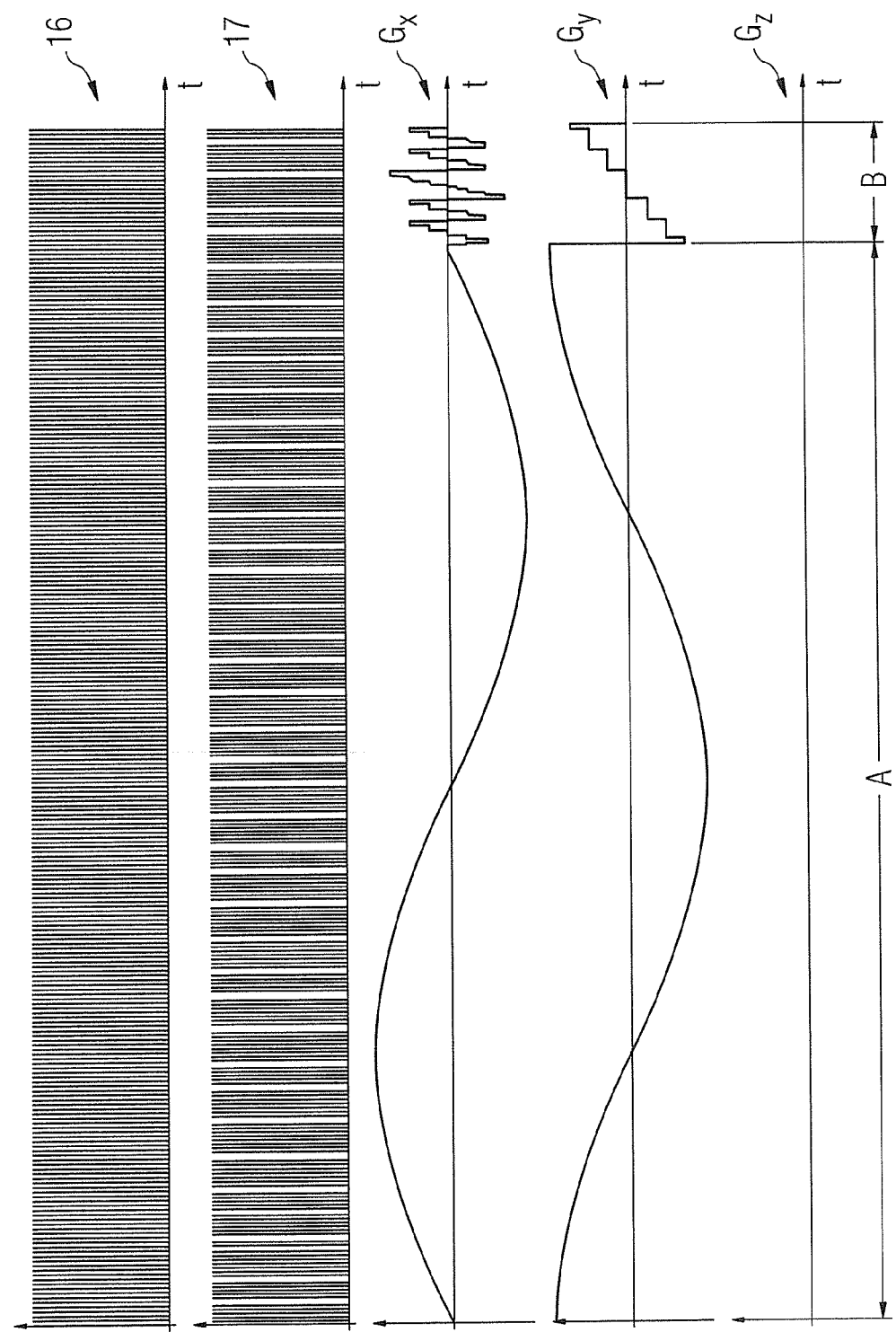
FIG. 6 schematically shows a sequence to acquire k-space corresponding to a projection image data set.

FIG. 6 schematically shows a sequence to acquire a raw data set to create a projection data set. The first line in FIG. 6 shows the radiated RF excitation pulses 16; the second line shows the associated readout time periods 17.

Here only two phase coding gradients are switched. A coding in the third direction—the slice direction, here the z-direction—is foregone ($G_z$=0).

As noted above, the echo times t1 (and possibly t2) are limited at the bottom only by the hardware constant $TE_{HW}$, and very short echo times can thus be achieved. This is independent of the switching of two or three phase coding gradients.

The phase coding gradients in the x-direction and y-direction are equal—$G_x$=sin(φ) or, respectively, $G_y$=cos(φ)—wherein φ is, for example, increased by the angle 360°/(number of projections $N_{Proj}$) at each radial k-space trajectory (beginning at φ=0) until 360° have been achieved. Overall, $N_{Proj}$ radial projections—i.e. $N_{Proj}$ radial k-space trajectories—are thus acquired for the projection data set. This is shown in the region "A" in FIG. 6, wherein 250 radial k-space trajectories are read out there.

As is apparent, in this way the phase coding gradients varies [sic] continuously between the radiation of a first RF excitation pulse to acquire raw data points of k-space corresponding to the imaging area and a second RF excitation pulse to acquire additional raw data points of k-space corresponding to the imaging area, which—as described above—contributes to a particularly low-noise acquisition of the raw data. This type of switching of the phase coding gradients also continues to be maintained in the region "B" described below.

$N_{Proj}$ is at 250 since this is the order of magnitude which is required in order to create a qualitatively high-grade projection image. Depending on resolution, maximum gradient strength and other factors, the proportion of k-space points to be scanned in a Cartesian manner amounts to approximately 1% to 20% of k-space to be acquired overall. In FIG. 6 the readout of Cartesian k-space points by means of a single point imaging method is shown in region "B". As mentioned above, it is not necessary to read out the k-space points of the region of the k-space center after the k-space points to be read out radially; rather, this can occur at an arbitrary point in time in the sequence.

If a repetition time TR (time between two RF excitation pulses) of 1 ms is assumed and a proportion of Cartesian k-space points $N_{Cart}$ of 10% of the radially read-out k-projections is assumed ($N_{Cart}$=0.1*$N_{Proj}$), a measurement time for a raw data set corresponding to a projection data set results:

$$(N_{Proj}+N_{Cart})*TR=1,1*N_{Proj}*1 \text{ ms}=275 \text{ ms}.$$

The acquisition is thus fast enough in order to be shown with time resolution at a presentation device.

If it is desired to show time-resolved images, the temporal resolution can additionally be increased in that k-space values are reused for two successive projection images. Portions of k-space then do not need to be re-measured in successive repetitions and the measurement time per image decreases.

If (according to an exemplary embodiment described above) a second echo is acquired after an echo time t2>t1 in order to be able to acquire a second projection image data set BD2 and calculate a difference image DBD, the repetition time TR increases, and therefore the measurement time for the raw data sets RD1 and RD2 corresponding to a respective projection data set BD1 and BD2 also increases by approximately a factor of two.

For example, one possible application of the time-resolved presentation lies in the field of orthopedics, wherein a patient moves joints (for example a wrist or knee etc.) to be examined in the measurement space of the magnetic resonance system during the acquisition of the measurement data. The movement of the ligaments and bones of the joint could thereby be observed instantaneously at the presentation device.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method to generate an image data set of an image area located in a measurement volume of a magnetic resonance system, said magnetic resonance system comprising a gradient system and an RF transmission/reception system, said method comprising:

reading out k-space corresponding to the imaging area, by:
(a) activating at least two phase coding gradients in respective spatial directions with said gradient system,
(b) after the activated phase coding gradients achieve a full strength, radiating a non-slice-selective RF excitation pulse with said RF transmission/reception system,
(c) after a time t1 following the radiated excitation pulse, acquiring echo signals with said RF transmission/reception system and storing said echo signals as raw data points in k-space along a radial k-space trajectory that is predetermined by the strength of the phase coding gradients, (d) repeating (a) through (c) with respectively different phase coding gradients in each repetition until k-space corresponding to the image area is read out in a first region of k-space along radial k-space trajectories, depending on said time t1, and (e) reading out a remainder of k-space that corresponds to the imaging area, said remainder not being filled by said first region and including at least a center of k-space, in a read out procedure that is different from (a) through (d), and storing all data points read out in (d) and (e); and reconstructing image data from the read out data points in k-space by implementing a reconstruction algorithm in a computerized processor, said reconstruction algorithm comprising a Fourier transformation of said data points.

2. The method as claimed in claim 1, comprising reading out raw data points in said remainder in (e) as Cartesian raw data points.

3. The method as claimed in claim 1, comprising reading out the raw data points in (e) using a single point imaging technique.

4. The method as claimed in claim 1, wherein said RF transmission/reception system has a minimum switchover time between operation in a transmission mode, in which said RF excitation pulse is radiated, and a reception mode, in which said echo signals are read out, and setting said time t1 equal to said minimum switchover time.

5. The method as claimed in claim 1, comprising radiating a plurality of said non-slice-selective RF excitation pulses, and varying said phase coding gradients continuously between radiation of a first of said non-selective RF excitation pulses to acquire k-space corresponding to raw data points of the imaging area, and a second of said RF excitation pulses to acquire additional raw data points of k-space corresponding to said image area.

6. The method as claimed in claim 1, comprising activating at least three phase coding gradients to acquire said raw data as a three-dimensional raw data set, from which a three-dimensional image data set is reconstructed.

7. The method as claimed in claim 1, comprising activating exactly two phase coding gradients to acquire a set of raw data representing a projection image data set.

8. The method as claimed in claim 1, comprising radiating multiple RF excitation pulses and, after each RF excitation pulse, acquiring at least one additional echo signal at a time t2, which is larger than t1, after each RF excitation pulse, and storing the second echo signal as an additional raw data point in k-space.

9. The method as claimed in claim 8, comprising reconstructing an additional image data set from each of the additional raw data points, using a Fourier transformation.

10. The method as claimed in claim 9, comprising calculating a difference image in said processor from said image data set and said additional image data set.

11. The method as claimed in claim 10, comprising forming said difference image with a weighting of one of said image data set and said additional image data set dependent on a time constant that exists in said imaging area.

12. A magnetic resonance system comprising:

a basic field magnet having an imaging area having a measurement volume adapted to receive an examination subject therein;

a gradient system;

an RF transmission/reception system; and a computerized control and evaluation system configured to: read out k-space corresponding to the imaging area, by (a) activating at least two phase coding gradients in respective spatial directions with said gradient system, (b) after the activated phase coding gradients achieve a full strength, radiating a non-slice-selective RF excitation pulse with said RF transmission/reception system, (c) after a time t1 following the radiated excitation pulse, acquiring echo signals with said RF transmission/reception system and storing said echo signals as raw data points in k-space along a radial k-space trajectory that is predetermined by the strength of the phase coding gradients, (d) repeating (a) through (c) with respectively different phase coding gradients in each repetition until k-space corresponding to the image area is read out in a first region of k-space along radial k-space trajectories, depending on said time t1, and (e) reading out a remainder of k-space that corresponds to the imaging area, said remainder not being filled by said first region and including at least a center of k-space, in a read out procedure that is different from (a) through (d), and storing all data points read out in (d) and (e); and reconstruct image data from the read out data points in k-space by implementing a reconstruction algorithm in a computerized processor, said reconstruction algorithm comprising a Fourier transformation of said data points.

13. A non-transitory, computer-readable storage medium encoded with programming instructions for operating a magnetic resonance system comprising a gradient system and an RF transmission/reception system and a computerized control and evaluation system, to generate an image data set of an imaging area located in a measurement volume of the magnetic resonance system, said programming instructions causing said computerized control and evaluation system to:

read out k-space corresponding to the imaging area, by:

(a) activating at least two phase coding gradients in respective spatial directions with said gradient system, (b) after the activated phase coding gradients achieve a full strength, radiating a non-slice-selective RF excitation pulse with said RF transmission/reception system, (c) after a time t1 following the radiated excitation pulse, acquiring echo signals with said RF transmission/reception system and storing said echo signals as raw data points in k-space along a radial k-space trajectory that is predetermined by the strength of the phase coding gradients, (d) repeating (a) through (c) with respectively different phase coding gradients in each repetition until k-space corresponding to the image area is read out in a first region of k-space along radial k-space trajectories, depending on said time t1, and (e) reading out a remainder of k-space that corresponds to the imaging area, said remainder not being filled by said first region and including at least a center of k-space, in a read out procedure that is different from (a) through (d), and storing all data points read out in (d) and (e); and reconstruct image data from the read out data points in k-space by implementing a reconstruction algorithm in a computerized processor, said reconstruction algorithm comprising a Fourier transformation of said data points.

* * * * *